Patent 4,596,815 — Kraatz et al., Jun. 24, 1986

[54] ANTIFUNGAL AZOLYLMETHYL-THIENYL-CARBINOL DERIVATIVES

[75] Inventors: Udo Kraatz, Leverkusen; Graham Holmwood, Wuppertal; Karl H. Büchel, Burscheid; Hans-Jürgen Rosslenbroich, Monheim; Hans Scheinpflug, Leverkusen, all of Fed. Rep. of Germany

[73] Assignee: Bayer Aktiengesellschaft, Leverkusen, Fed. Rep. of Germany

[21] Appl. No.: 614,598

[22] Filed: May 29, 1984

[30] Foreign Application Priority Data

Jun. 11, 1983 [DE] Fed. Rep. of Germany ....... 3321158

[51] Int. Cl.$^4$ .................. A01N 43/653; C07D 409/06
[52] U.S. Cl. ..................................... 514/383; 514/184; 548/101; 548/262; 549/60; 549/70; 549/73
[58] Field of Search ................ 548/262, 101; 514/184, 514/283

[56] References Cited

FOREIGN PATENT DOCUMENTS

| 0040345 | 11/1981 | European Pat. Off. ............ 548/262 |
| 0046337 | 2/1982 | European Pat. Off. ............ 546/276 |
| 0061835 | 10/1982 | European Pat. Off. ............ 548/262 |

Primary Examiner—Alton D. Rollins
Attorney, Agent, or Firm—Sprung Horn Kramer & Woods

[57] ABSTRACT

Azolylmethyl-thienyl-carbinols of the formula

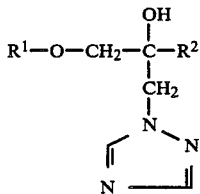

in which
$R^1$ is optionally substituted phenyl, and
$R^2$ is optionally substituted thienyl,
or addition products thereof with acids or metal salts, which possess fungicidal activity.

12 Claims, No Drawings

ANTIFUNGAL AZOLYLMETHYL-THIENYL-CARBINOL DERIVATIVES

The present invention relates to new azolylmethyl-thienyl-carbinol derivatives, a process for their preparation and their use as fungicides.

It has already been disclosed that certain hydroxyethylazolyl derivatives, such as, for example, 1-(2,4-dichlorophenoxy)- or 1-phenoxy-3,3-dimethyl-2-(1,2,4-triazol-1-yl-methyl)-butan-2-ol and 1-(4-chlorophenoxy)-2-(4-chlorophenyl)- or -2-(2,4-dichlorophenyl)-3-(1,2,4-triazol-1-yl)-propan-2-ol, have good fungicidal properties (see European Pat. No. 0,040,345). However, the action of these compounds is not always completely satisfactory in all ranges of indication, particularly when low amounts or concentrations are used.

New azolylmethyl-thienyl-carbinol derivatives of the general formula

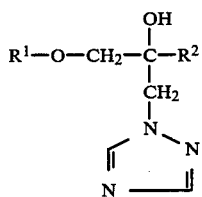

in which
$R^1$ represents optionally substituted phenyl and
$R^2$ represents optionally substituted thienyl,
have been found.

The compounds of the formula (I) possess as asymmetric carbon atom and can therefore occur in the forms of the two optical isomers.

Furthermore, it has been found that the azolyl-methyl-thienyl-carbinol derivatives of the formula (I) are obtained when oxiranes of the formula

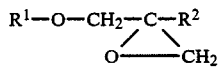

in which
$R^1$ represents optionally substituted phenyl and
$R^2$ represents optionally substituted thienyl,
are reacted with azoles of the formula

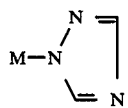

in which
M represents hydrogen, sodium, potassium or an ammonium cation ($NR_4^\oplus$),
in the presence of a diluent and, if appropriate, in the presence of a base.

If required, the resulting compounds of the formula (I) can subsequently be subjected to an additional reaction with an acid or a metal salt.

The new azolylmethyl-thienyl-carbinol derivatives of the formula (I) have powerful fungicidal properties. Moreover, the compounds according to the invention surprisingly exhibit a better fungicidal activity than the compounds 1-(2,4-dichlorophenoxy)- or 1-phenoxy-3,3-dimethyl-2-(1,2,4-triazol-1-yl-methyl)-butan-2-ol and 1-(4-chlorophenoxy)-2-(4-chlorophenyl)- or -2-(2,4-dichlorophenyl)-3-(1,2,4-triazol-1-yl)-propan-2-ol, which are known from the prior art and are similar compounds constitutionally and in terms of their action. The substances according to the invention thus represent an enrichment of the art.

In addition, the new azolylmethyl-thienyl-carbinol derivatives are interesting intermediate products. Thus, for example, the compounds of the general formula (I) can be converted at the hydroxyl group to the corresponding ethers in a conventional manner. Furthermore, acyl or carbamoyl derivatives of the compounds of the general formula (I) can be obtained by reaction with, for example, acyl halides or carbamoyl chlorides in a manner which is known in principle.

Formula (I) gives a general definition of the azolylmethyl-thienyl-carbinol derivatives according to the invention. In this formula,
$R^1$ preferably represents phenyl which is optionally monosubstituted to trisubstituted by identical or different substituents, the following being mentioned as substituents: halogen, alkyl having 1 to 4 carbon atoms, and alkoxy and alkylthio, each having 1 or 2 carbon atoms; halogenoalkyl, halogenoalkoxy and halogenoalkylthio, each having 1 or 2 carbon atoms and 1 to 5 identical or different halogen atoms, such as fluorine atoms and chlorine atoms, cycloalkyl having 5 or 6 carbon atoms, and optionally halogen-substituted phenyl; and
$R^2$ preferably represents thienyl which is monosubstituted to trisubstituted by identical or different substituents, the following being mentioned as substituents: halogen and alkyl having 1 to 4 carbon atoms.

Particularly preferred compounds of the formula (I) are those in which
$R^1$ represents phenyl which is optionally mono-substituted or disubstituted by identical or different substituents, the following being mentioned as substituents: fluorine, chlorine, methyl, tert.-butyl, methoxy, trifluoromethyl, trifluoromethoxy, phenyl and chlorophenyl; and
$R^2$ represents thienyl which is monosubstituted or disubstituted by identical or different substituents, the following being mentioned as substituents: chlorine, bromine, methyl and ethyl.

Preferred compounds according to the invention are also addition products of acids and those azolylmethyl-thienyl-carbinol derivatives of the formula (I) in which the substituents $R^1$ and $R^2$ have the meanings which have already been mentioned for these substituents as being preferred.

Acids with which adducts can be formed preferably include hydrohalic acids, such as, for example, hydrochloric acid and hydrobromic acid, in particular hydrochloric acid, and also phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, as well as sulphonic acids, such as p-toluenesulphonic acid and naphthalene-1,5-disulphonic acid.

Other preferred compounds according to the invention are addition products of salts of metals of main group II to IV and of sub-group I and II and IV to VIII and those azolylmethyl-thienyl-carbinol derivatives of the formula (I) in which the substituents $R^1$ and $R^2$ have the meanings which have already been mentioned for these substituents as being preferred.

Amongst these, salts of copper, zinc, manganese, magnesium, tin, iron and nickel are particularly preferred. Suitable anions of these salts are those which are derived from those acids which lead to physiologically tolerated addition products. Particularly preferred acids of this type in this connection are the hydrohalic acids, such as, for example, hydrochloric acid and hydrobromic acid, nitric acid and sulphuric acid.

If, for example, 2-(2-bromothien-5-yl)-2-(4-chlorophenoxymethyl)-oxirane and 1,2,4-triazole are used as starting materials, the course of the process according to the invention can be represented by the following equation:

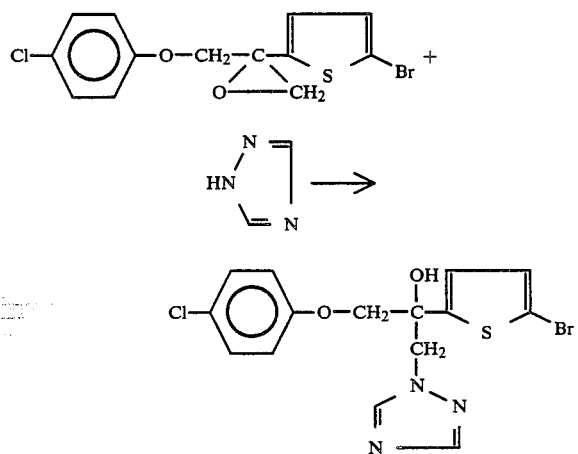

Formula (II) gives a general definition of the oxiranes to be used as starting materials for carrying out the process according to the invention. In this formula, $R^1$ and $R^2$ preferably have the meanings which have already been mentioned in connection with the description of the substances according to the invention of the formula (I), as being preferred for these substituents.

The oxiranes of the formula (II) were unknown hitherto. However, they can be obtained in a generally known manner by reacting ketones of the formula $$R^1-O-CH_2-CO-R^2 \qquad (IV)$$

either (α) with dimethyloxosulphonium methylide of the formula

(V)

in a manner which is in itself known, in the presence of a diluent, such as, for example, dimethyl sulphoxide, at temperatures between 20° and 80° C. (in this context, see the data in J. Am. Chem. Soc. 87, 1363–1364 (1965), or (β) with trimethylsulphonium methylsulphate of the formula

(VI)

in a manner which is in itself known, in the presence of an inert organic solvent, such as, for example, acetonitrile, and in the presence of a base, such as, for example, sodium methylate, at temperatures between 0° and 60° C., preferably at room temperature (also see the data in Heterocycles 8, 397 (1977)).

The ketones of the formula (IV) were likewise hitherto unknown. They too can be obtained in a generally known manner by reacting halogenoacetyl-thiophenes with appropriate phenols in the presence of an inert organic solvent, such as, for example, acetone, and in the presence of a base, such as, for example, potassium carbonate, preferably at the reflux temperature (also see the preparation examples).

Suitable diluents for the process according to the invention are organic solvents which are inert under the reaction conditions. These preferably include alcohols, such as, for example, ethanol, methoxyethanol or propanol; ketones, such as, for example, butan-2-one; nitriles, such as, for example, acetonitrile; esters, such as, for example, ethyl acetate; ethers, such as, for example, dioxane; aromatic hydrocarbons, such as, for example, benzene and toluene; or amides, such as, for example, dimethylformamide.

Suitable bases for the reaction according to the invention are all inorganic and organic bases which can be customarily used. These preferably include alkali metal carbonates, such as, for example, sodium carbonate and potassium carbonate; alkali metal hydroxides, such as, for example, sodium hydroxide; alkali metal alcoholates, such as, for example, sodium methylate, potassium methylate, sodium ethylate and potassium ethylate; alkali metal hydrides, such as, for example, sodium hydride; and lower tertiary alkylamines, cycloalkylamines, and aralkylamines, such as, in particular, triethylamine.

In carrying out the process according to the invention, the reaction temperatures can be varied within a relatively wide range. In general, the reaction is carried out at temperatures between 0° and 200° C., preferably between 60° and 150° C.

In carrying out the process according to the invention, 1 to 2 mol of the azole of the formula (III) and, if appropriate, 1 to 2 mols of a base are preferably employed per mols of the oxirane of the formula (II); the end products are isolated in a generally known manner.

The acid addition salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtration, and, if appropriate, purified by washing with an inert organic solvent.

The metal salt complexes of compounds of the formula (I) can be obtained in a simple manner by customary processes, as, for example, by dissolving the metal salt in alcohol, for example ethanol, and adding the solution to compounds of the formula (I). Metal salt complexes can be isolated in a known manner, for example by filtration, and, if appropriate, purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations reouired for combating plant diseases, permits treatment of above-ground parts of plants, of vegetative propagation stock and seeds and of the soil.

As plant protection agents, the active compounds according to the invention can be used with particularly good success for combating rice diseases, such as *Pyricularia oryzae*; cereal diseases, such as powdery mildew, rust, *Cochliobolus sativus* and *Pyrenophora teres*; and against apple scab and bean rust.

It should be emphasized that the substances according to the invention not only display a protective action but in some cases also have a systemic action. Thus, it is possible to protect plants against infestation by fungi if the active compounds are fed to the above-ground parts of the plant via the soil and the root or via the seed.

The active compounds can be converted to the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strong polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic oolymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.0001 to 0.02% by weight are required at the place of action.

PREPARATION EXAMPLES

EXAMPLE 1

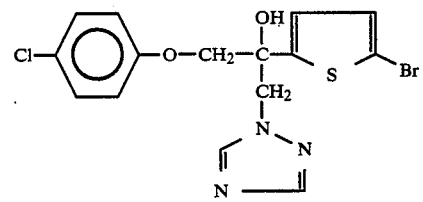

16 g of crude 2-(2-bromo-thien-5-yl)-2-(4-chlorophenoxymethyl)-oxirane in 200 ml of acetonitrile are heated under reflux with 11 g (0.157 mol) of 1,2,4-triazole and 5 g of potassium carbonate for 4 hours. Thereafter, the reaction mixture is poured onto water, and extracted with methylene chloride. The methylene chloride phase is dried over sodium sulphate and evaporated down in vacuo. The residue is chromatographed over silica gel using the chloroform/ethyl acetate (1:1) system. 10.5 g (55% of theory) of 2-(2-bromo-thien-5-yl)-1-(4-chlorophenoxy)-3-(1,2,4-triazol-1-yl)-propan-2-ol are obtained in the form of a yellow resin which crystallizes after standing for a long time. Melting point 108°–112° C.

PREPARATION OF THE STARTING MATERIAL

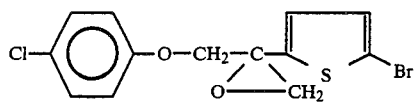

1.5 g (0.05 mol) of 80% strength sodium hydride are added in portions to a suspension of 11 g (0.05 mol) of trimethylsulphonium iodide in 100 ml of dimethyl sulphoxide under a nitrogen atmosphere, and the mixture is stirred for a further 30 minutes at room temperature. A solution of 15.5 g (0.046 mol) of 2-bromo-thien-5-yl 4-chlorophenoxymethyl ketone in a small amount of dimethyl sulphoxide is then added dropwise, and the mixture is heated to 60° C. for 1 hour. The reaction mixture is then poured onto water, and extracted with methylene chloride. The organic phase is washed several times with water, dried over magnesium sulphate and evaporated down. Crude 2-(2-bromo-thien-5-yl)-2-(4-chlorophenoxymethyl)-oxirane is obtained as a viscous oil, which is directly reacted further.

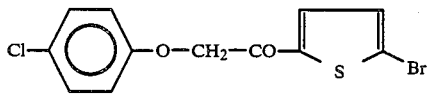

28.4 g (0.1 mol) of 2-bromoacetyl-5-bromothiophene are heated under reflux with 19.3 g (0.15 mol) of 4-chlorophenol and 27.6 g (0.2 mol) of potassium carbonate in 200 ml of ketone for 3 hours, while stirring. The mixture is then poured into water, and the ether-ketone is extracted with methylene chloride. The organic phase is washed with dilute sodium hydroxide solution and then with water, and is dried over magnesium sulphate. After the organic phase has been evaporated down, the residue is recrystallized from ethanol. 17.3 g (52% of theory) of 2-bromo-thien-5-yl 4-chlorophenoxymethyl ketone of melting point 128°–130° C. are obtained.

The following compounds of the general formula

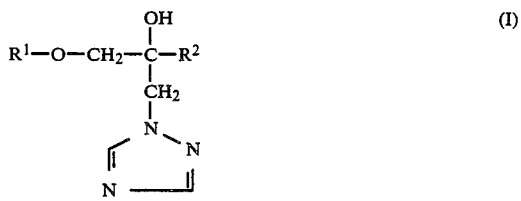

are obtained in a similar manner and by the process described:

| Example No. | R¹ | R² | Melting point (°C.) or Rf-value (CDCl₃/ethyl acetate 4:1) |
|---|---|---|---|
| 2 | phenyl | 2,5-dimethylthien-3-yl | [0.19] |
| 3 | 4-chlorophenyl | 2,5-dimethylthien-3-yl | [0.18] |
| 4 | 4-chloro-2-methylphenyl | 2,5-dimethylthien-3-yl | 112–14 |
| 5 | 2,4-dichlorophenyl | 2,5-dimethylthien-3-yl | 142 |
| 6 | 2,4-dichlorophenyl | 2,5-dichlorothien-3-yl | [0.22] |

The compounds shown below are employed as comparative substances in the examples which follow:

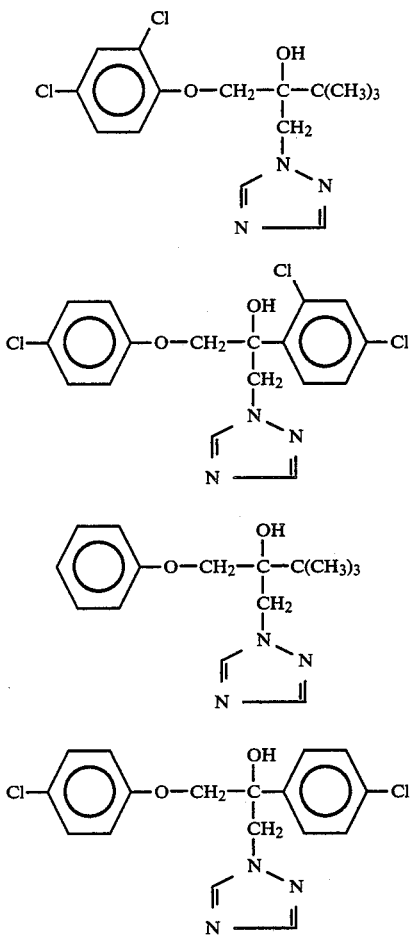

EXAMPLE A

Pyricularia Test (Rice)/Protective

Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for protective activity, young rice plants are sprayed with the preparation of active compound until dripping wet. After the spray coating has dried off, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: 1, 2, 3, 4 and 6.

EXAMPLE B

Pyricularia Test (Rice)/Systemic

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 2, 3, 4, 5, 6 and 1.

It is understood that the specification and examples are illustrative but not limitative of the present invention and that other embodiments within the spirit and scope of the invention will suggest themselves to those skilled in the art.

We claim:

1. An azolylmethyl-thienyl-carbinol of the formula

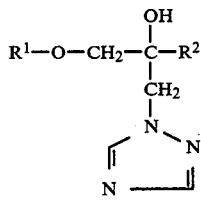

in which
R$^1$ is phenyl which is optionally monosubstituted to trisubstituted by halogen, alkyl having 1 to 4 carbon atoms, alkoxy or alkylthio, each having 1 or 2 carbon atoms, halogenoalkyl, halogenoalkoxy or halogeno-alkylthio each having 1 or 2 carbon atoms and 1 to 5 identical or different halogen atoms, cycloalkyl having 5 or 6 carbon atoms and/or optionally halogen-substituted phenyl, and
R$^2$ is thienyl which is optionally monosubstituted to trisubstituted by halogen and/or alkyl having 1 to 4 carbon atoms, or an addition product thereof with an acid or metal salt.

2. A compound or addition product according to claim 1, in which
R$^1$ is phenyl which is optionally monosubstituted or disubstituted by chlorine and/or methyl, and
R$^2$ is thienyl which is optionally monosubstituted or disubstituted by chlorine, bromine and/or methyl.

3. A compound or addition product according to claim 1, in which
R$^1$ is phenyl which is optionally monosubstituted or disubstituted by fluorine, chlorine, methyl, tert.-butyl, methoxy, trifluoromethyl, trifluoromethoxy, phenyl and/or chlorophenyl, and
R$^2$ is thienyl which is optionally monosubstituted or disubstituted by chlorine, bromine, methyl and/or ethyl.

4. A compound according to claim 1, wherein such compound is 2-(2-bromo-thien-5-yl)-1-(4-chlorophenoxy)-3-(1,2,4-triazol-1-yl)-propan-2-ol of the formula

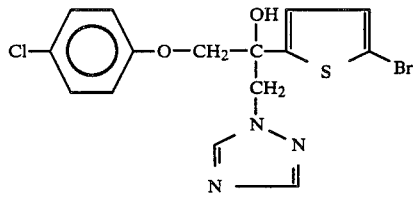

or an addition product thereof with an acid or metal salt.

5. A compound according to claim 1, wherein such compound is 2-(2,5-dimethyl-thien-4-yl)-1-phenoxy-3-(1,2,4-triazol-1-yl)-propan-2-ol of the formula

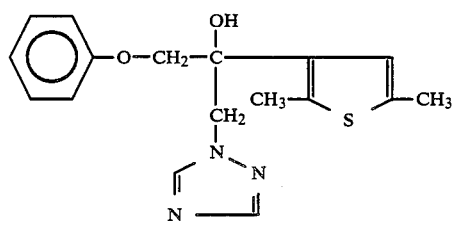

or an addition product thereof with an acid or metal salt.

6. A compound according to claim 1, wherein such compound is 2-(2,5-dimethyl-thien-4-yl)-1-(4-chlorophenoxy)-(1,2,4-triazol-1-yl)-propan-2-ol of the formula

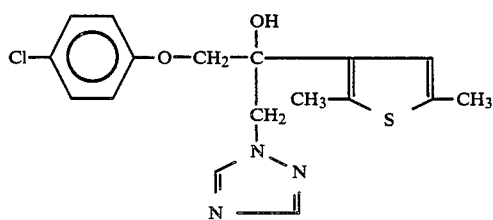

or an addition product thereof with an acid or metal salt.

7. A compound according to claim 1, wherein such compound is 2-(2,5-dimethyl-thien-4-yl)-1-(4-chloro-2-methylphenoxy)-3-(1,2,4-triazol-1-yl-propan-2-ol of the formula

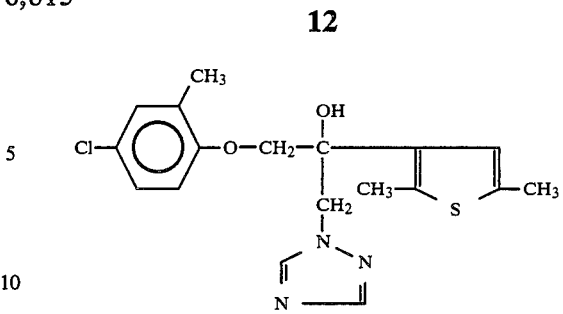

or an addition product thereof with an acid or metal salt.

8. A compound according to claim 1, wherein such compound is 2-(2,5-dimethyl-thien-4-yl)-1-(2,4-dichlorophenoxy)-3-(1,2,4-triazol-1-yl)-propan-2-ol of the formula

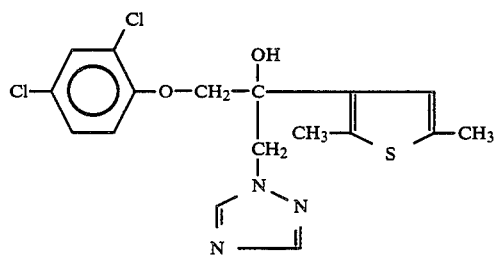

or an addition product thereof with an acid or metal salt.

9. A compound according to claim 1, wherein such compound is 2-(2,5-dichloro-thien-4-yl)-1-(2,4-dichlorophenoxy)-3-(1,2,4-triazol-1-yl)-propan-2-ol of the formula

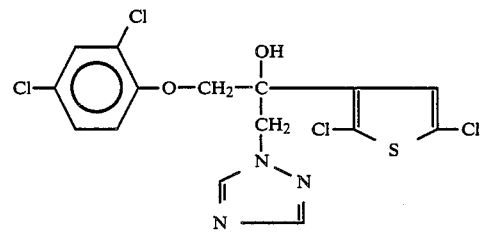

or an addition product thereof with an acid or metal salt.

10. A fungicidal composition comprising a fungicidally effective amount of a compound or addition product according t0 claim 1 in admixture with a diluent.

11. A method of combatting fungi which comprises administering to such fungi or to a habitat thereof a fungicidally effective amount of a compound or addition product according to claim 1.

12. The method according to claim 11, wherein such compound is
2-(2-bromo-thien-5-yl)-1-(4-chlorophenoxy)-3-(1,2,4-triazol-1-yl)-propan-2-ol,
2-(2,5-dimethyl-thien-4-yl)-1-phenoxy-3-(1,2,4-triazol-1-yl)-propan-2-ol,
2-(2,5-dimethyl-thien-4-yl)-1-(4-chlorophenoxy)-3-(1,2,4-triazol-1-yl)-propan-2-ol,
2-(2,5-dimethyl-thien-4-yl)-1-(4-chloro-2-methylphenoxy)-3-(1,2,4-triazol-1-yl)-propan-2-ol,
2-(2,5-dimethyl-thien-4-yl)-1-(2,4-dichlorophenoxy)-3-(1,2,4-triazol-1-yl)-propan-2-ol or
2-(2,5-dichloro-thien-4-yl)-1-(2,4-dichlorophenoxy)-3-(1,2,4-triazol-1-yl)-propan-2-ol,
or an addition product thereof with an acid or metal salt.

* * * * *